(12) United States Patent
Hayakawa et al.

(10) Patent No.: US 10,295,626 B2
(45) Date of Patent: May 21, 2019

(54) MRI APPARATUS

(71) Applicant: TOSHIBA MEDICAL SYSTEMS CORPORATION, Otawara-Shi, Tochigi-Ken (JP)

(72) Inventors: Hiroshi Hayakawa, Tochigi (JP); Tomoyuki Yoshida, Tochigi (JP); Sadanori Tomiha, Tochigi (JP); Kazuyuki Soejima, Tochigi (JP)

(73) Assignee: TOSHIBA MEDICAL SYSTEMS CORPORATION, Otawara-shi, Tochigi-Ken (JP)

( * ) Notice: Subject to any disclaimer, the term of this patent is extended or adjusted under 35 U.S.C. 154(b) by 480 days.

(21) Appl. No.: 14/976,212

(22) Filed: Dec. 21, 2015

(65) Prior Publication Data

US 2016/0109541 A1 Apr. 21, 2016

Related U.S. Application Data

(63) Continuation of application No. PCT/JP2014/066203, filed on Jun. 18, 2014.

(30) Foreign Application Priority Data

Jun. 21, 2013 (JP) .................. 2013-130974

(51) Int. Cl.
*G01R 33/36* (2006.01)
*G01R 33/3415* (2006.01)
(Continued)

(52) U.S. Cl.
CPC ..... *G01R 33/3692* (2013.01); *G01R 33/3415* (2013.01); *G01R 33/3621* (2013.01); *A61B 5/0024* (2013.01); *A61B 5/055* (2013.01)

(58) Field of Classification Search
None
See application file for complete search history.

(56) References Cited

U.S. PATENT DOCUMENTS 4,975,644 A * 12/1990 Fox .................. G01R 33/3415
 324/318
5,572,130 A * 11/1996 Ratzel ............... G01R 33/3415
 324/318
(Continued)

FOREIGN PATENT DOCUMENTS

JP  2007-203036  8/2007
JP  2008-518652  6/2008
(Continued)

OTHER PUBLICATIONS

English Translation of International Preliminary Report on Patentability dated Dec. 22, 2015 for Application No. PCT/JP2014/066203.
(Continued)

*Primary Examiner* — Melissa J Koval
*Assistant Examiner* — Nasima Monsur
(74) *Attorney, Agent, or Firm* — Nixon & Vanderhye P.C.

(57) ABSTRACT

In one embodiment, an MRI apparatus includes receiving coils each including an A/D converter configured to convert an MR signal received from an object into a digital signal by sampling the MR signal, a clock generation circuit configured to generate a reference clock of the sampling, and a radio transmission circuit configured to wirelessly transmit a digitized MR signal; and a main body configured to wirelessly receive the digitized MR signal and generate an image of the object by reconstructing the digitized MR signal, wherein one of the receiving coils selected as a reference receiving coil by the main body is configured to transmit the reference clock to each of other receiving coils by radio or by wire; and each of the other receiving coils is (Continued)

configured to synchronize the reference clock generated by the clock generation circuit with the reference clock transmitted from the reference receiving coil.

20 Claims, 16 Drawing Sheets

(51) Int. Cl.
    *A61B 5/055*     (2006.01)
    *A61B 5/00*     (2006.01)

(56) References Cited

U.S. PATENT DOCUMENTS

| | | |
|---|---|---|
| 2009/0267600 A1 | 10/2009 | Okamoto et al. |
| 2009/0267601 A1 | 10/2009 | Van Helvoort et al. |
| 2010/0259261 A1* | 10/2010 | Saes ............... G01R 33/341 324/309 |
| 2010/0308826 A1 | 12/2010 | Saes et al. |
| 2011/0080167 A1* | 4/2011 | Kannengisser .. G01R 33/56509 324/309 |
| 2011/0109316 A1* | 5/2011 | Akita ............... G01R 33/3607 324/322 |
| 2012/0001633 A1* | 1/2012 | Fuderer ............. G01R 33/5611 324/309 |

FOREIGN PATENT DOCUMENTS

| | | |
|---|---|---|
| JP | 2011-507588 | 3/2011 |
| JP | 2011-92553 | 5/2011 |

OTHER PUBLICATIONS

Int'l. Search Report for PCT/JP2014/066203 dated Jul. 29, 2014, four pages.

* cited by examiner

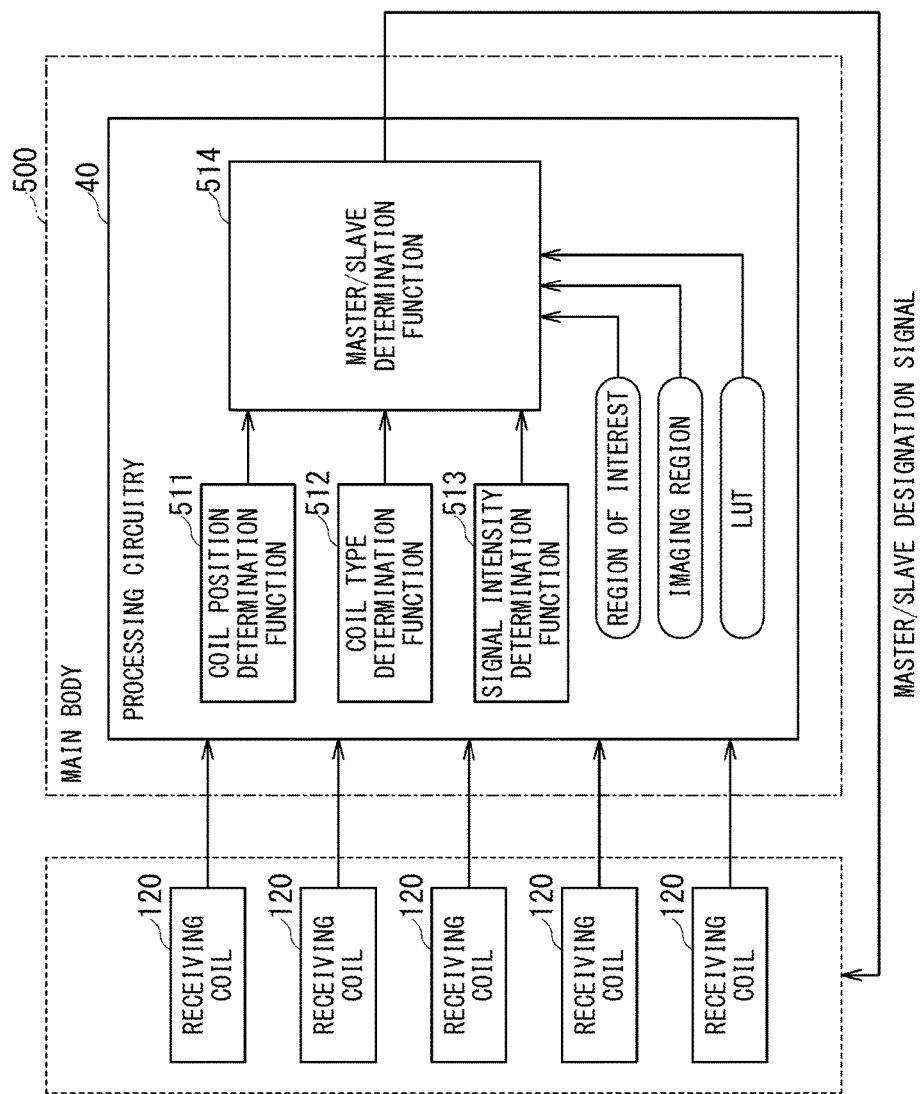

MRI APPARATUS

CROSS-REFERENCE TO RELATED APPLICATIONS

This application is a Continuation Application of No. PCT/JP2014/66203, filed on Jun. 18, 2014, and the PCT application is based upon and claims the benefit of priority from Japanese Patent Application No. 2013-130974, filed on Jun. 21, 2013, the entire contents of each of which are incorporated herein by reference.

FIELD

Embodiments described herein relate generally to an MRI (Magnetic Resonance Imaging) apparatus.

BACKGROUND

MRI is an imaging method in which nuclear spin of an object placed in a static magnetic field is excited by an RF (Radio Frequency) signal having the Larmor frequency and an image is reconstructed based on MR (Magnetic Resonance) signals emitted from the object due to the excitation.

In recent MRI apparatuses, multiple receiving coils are commonly used. The multiple receiving coils are arranged around an object and MR signals received by these receiving coils are subjected to signal processing in a signal processing system disposed in the subsequent stage. The above-described receiving coil is also referred to as a surface coil.

As the number of receiving coils increases, the number of cables wiring each of the receiving coils to the signal processing system increases and thus handling of these cables becomes complicated. Therefore, instead of wired transmission, technology to wirelessly transmit signal transmission from each of the receiving coils to the signal processing system has been developed.

Moreover, from the view point of improving transmission quality of MR signals, technology to digitize analogue MR signals received by the receiving coils not in the signal processing system disposed in the subsequent stage but in each of the receiving coils has been considered. In this technology, digitized MR signals are wirelessly transmitted from each of the receiving coils to the signal processing system.

In order to perform A/D (analogue to digital) conversion in each of the receiving coils, a clock for A/D conversion (hereinafter, referred to as a reference clock) is necessary in each of the receiving coils. In this case, the following two types of configuration are possible. The one of them is to dispose a generation means of the reference clock inside each of the receiving coils (hereinafter, referred to as configuration by built-in clock type receiving coils). The other of them is to generate the reference clock in the signal processing system and transmit this reference clock to each of the receiving coils from the signal processing system (hereinafter, referred to as configuration by non-built-in clock type receiving coils).

In the configuration by built-in clock type receiving coils, distance between a sampling position of MR signals and a generation means of the reference clock can be shortened as compared with the configuration by non-built-in clock type receiving coils. Thus, in the configuration by built-in clock type receiving coils, transmission quality of the transmitted reference clock is hardly decreased and MR signals can be sampled with a high-quality reference clock.

Meanwhile, in the configuration by built-in clock type receiving coils, it is necessary to synchronize the reference clock between the respective receiving coils.

However, an MRI apparatus, which is equipped with plural built-in clock type receiving coils and can synchronize the reference clock for each of the built-in clock type receiving coils, has not necessarily been sufficiently studied.

BRIEF DESCRIPTION OF THE DRAWINGS

FIG. 6 is a functional block diagram showing an example of configuration relevant to determination of the master receiving coil;

DETAILED DESCRIPTION

In one embodiment, an MRI apparatus includes a plurality of receiving coils each of which includes an A/D converter configured to convert an MR signal received from an object into a digital signal by sampling the MR signal, a clock generation circuit configured to generate a reference clock of the sampling, and a radio transmission circuit configured to wirelessly transmit a digitized MR signal; and a main body configured to wirelessly receive the digitized MR signal and generate an image of the object by reconstructing the digitized MR signal, wherein one of the plurality of receiving coils selected as a reference receiving coil by the main body is configured to transmit the reference clock to each of other receiving coils by radio or by wire; and each of the other receiving coils is configured to synchronize the reference clock generated by the clock generation circuit with the reference clock transmitted from the reference receiving coil.

Hereinafter, embodiments of the present invention will be explained by reference to the accompanied drawings.

(1) Overall Configuration

Figure 1:
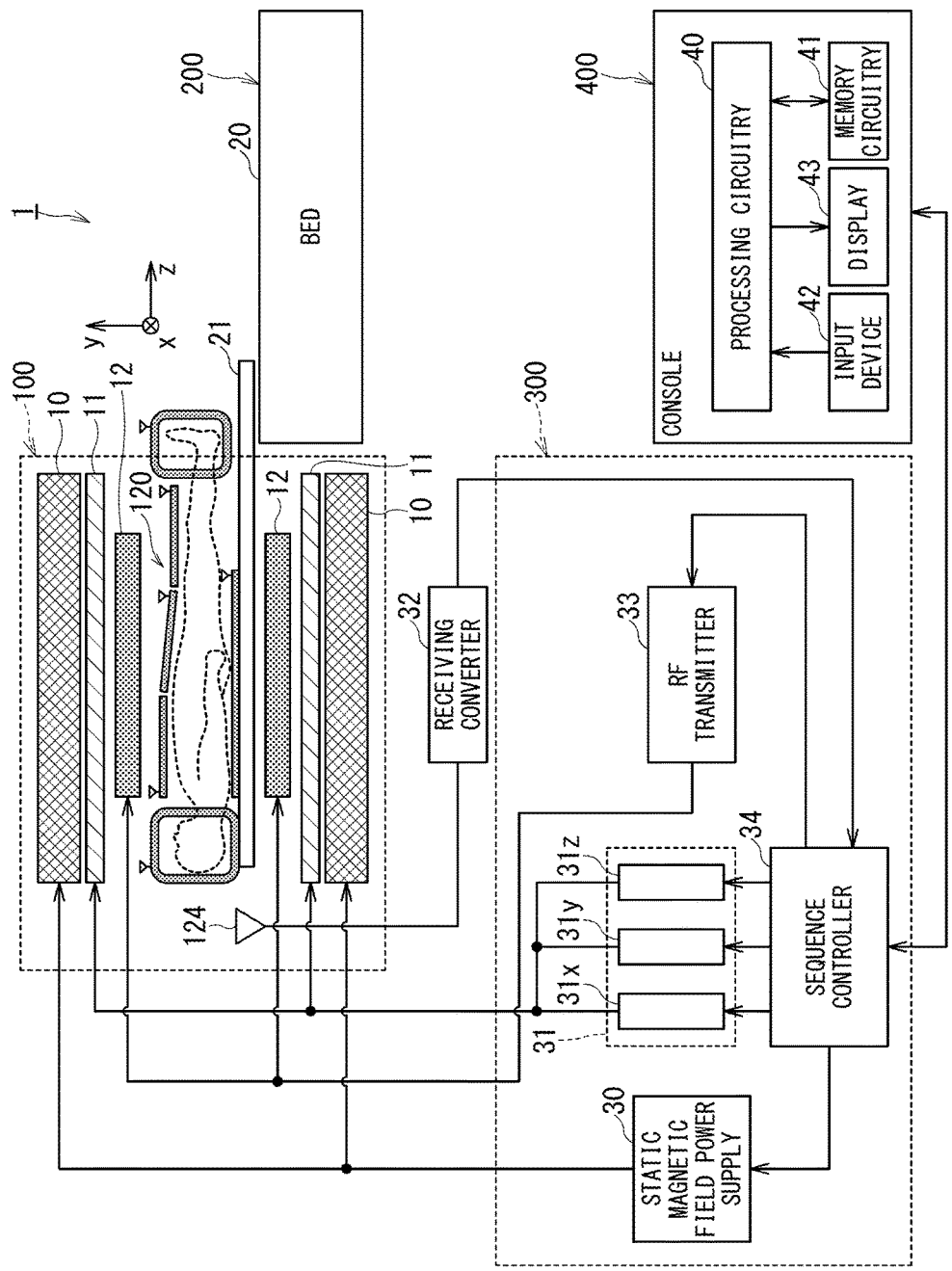
FIG. 1 is a block diagram showing an example of overall configuration of an MRI apparatus of each embodiment.

FIG. 1 is a block diagram showing an example of overall configuration of an MRI apparatus 1 of each embodiment. The MRI apparatus 1 includes a gantry 100, a bed 200, control cabinet components 300, a console 400, and the like.

The gantry 100 includes hardware components such as a static magnetic field magnet 10, a gradient coil 11, a whole body coil 12, and these components are housed in a cylindrical case. The bed 200 includes a bed body 20 and a table 21.

The control cabinet components 300 include a static magnetic field power supply 30, gradient coil power supplies 31, an RF transmitter 33, a sequence controller 34, and the like. The gradient coil power supplies 31 includes an X axis gradient coil power supply 31x, a Y axis gradient coil power supply 31y, and a Z axis gradient coil power supply 31z. In addition, the console 400 is configured as a computer including processing circuitry 40, memory circuitry 41, an input device 42, and a display 43.

The static magnetic field magnet 10 of the gantry 100 is substantially in the form of a cylinder. The static magnetic field magnet 10 generates a static magnetic field inside the bore, which is an internal space of the cylindrical structure thereof and functions as an imaging space for an object, such as a patient.

The static magnetic field magnet 10 includes a superconductive coil inside and the superconductive coil is cooled down to an extremely low temperature by liquid helium. The static magnetic field magnet 10 generates the static magnetic field by supplying the superconductive coil with the electric current provided from the static magnetic field power supply 30 in an excitation mode. Afterward, when the static magnetic field magnet 10 shifts to a permanent current mode, the static magnetic field power supply 30 is separated. Once it enters the permanent current mode, the static magnetic field magnet 10 continues to generate a strong static magnetic field for a long time, for example, over one year. Incidentally, the static magnetic field magnet 10 may be configured as a permanent magnet.

The gradient coil 11 is also substantially in the form of a cylinder and is fixed to the inside of the static magnetic field magnet 10. This gradient coil 11 applies gradient magnetic fields to the imaging space in the respective directions of the X axis, the Y axis, and the Z axis, by using the electric currents supplied from the above-described gradient coil power supplies 31x, 31y, and 31z.

The bed body 20 of the bed 200 can move the table 21 in the upward and downward directions, and moves the table 21 on which the object is loaded to a predetermined height before imaging. Afterward, at the time of imaging, the bed body 20 moves the table 21 in the horizontal direction so as to move the object inside the bore.

The whole body coil 12 is also substantially in the form of a cylinder. The whole body coil 12 applies RF pulses transmitted from the RF transmitter 33 to the object, according to a command from the sequence controller 34. In addition, the whole body coil 12 receives magnetic resonance signals (hereinafter, referred to MR signals) emitted from the object due to the application of the RF pulses. As mentioned above, the whole body coil 12 functions as a dual-purpose coil used for application of RF pulses and reception of MR signals.

Meanwhile, the MRI apparatus 1 includes receiving coils 120 arranged in proximity to the object as shown in FIG. 1 aside from the whole body coil 12, and these receiving coils 120 also receive MR signals emitted from the object.

As described above, the MRI apparatus 1 is configured to wirelessly transmit MR signals received by the whole body coil 12 and the receiving coils 120. The MR signals wirelessly transmitted from the receiving coils 120 and/or the whole body coil 12 are converted into raw data of the MR signals which are quadrature-detected I/Q (In-phase/Quadrature) digital signals of the baseband, and then transmitted to the sequence controller 34. Incidentally, the MRI apparatus 1 further includes a receiving converter 32. This receiving converter 32 may be disposed in the gantry 100 side or may be disposed in the control cabinet components 300 side.

The sequence controller 34 performs a scan of the object by driving each of the gradient coil power supplies 31 and the RF transmitter 33 under the control of the console 400. Afterward, when the sequence controller 34 receives the raw data as the result of the scan from the receiving converter 32, the sequence controller 34 transmits the raw data to the console 400.

The console 400 controls the entirety of the MRI apparatus 1. Specifically, the console 400 receives various types of information such as imaging conditions and commands inputted by a user such as an inspection engineer via input tools of the input device 42 such as a mouse and a keyboard.

Then, the processing circuitry 40 causes the sequence controller 34 to perform a scan based on the inputted imaging conditions, and reconstructs images based on the raw data transmitted from the sequence controller 34. The reconstructed images are stored in the memory circuitry 41 and displayed on the display 43.

Figure 2:
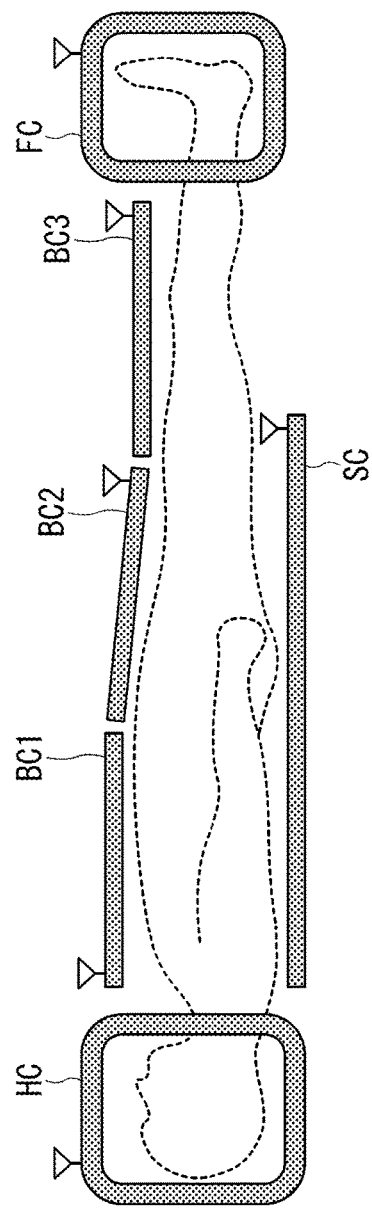
FIG. 2 is a schematic diagram showing an example of one set of receiving coils shown in FIG. 1.

FIG. 2 is a schematic diagram showing an example of one set of the receiving coils 120 shown in FIG. 1. In the example of FIG. 2, a head coil HC attached to the head, a spine coil SC attached to the back side, body coils BC1, BC2, and BC3 attached to the ventral side, and a foot coil FC attached to the foot are shown as six receiving coils 120.

The MRI apparatus 1 selects one of these receiving coils 120 (HC, SC, BC1, BC2, BC3, and FC), and determines the selected one as the master receiving coil 120M which is also referred to as a reference receiving coil 120M. Moreover, the MRI apparatus 1 determines all the other receiving coils 120 except the master receiving coil 120M as the slave receiving coils 120S. A method of selecting the master receiving coil 120M from the plural receiving coils 120 will be described below.

Figure 3:
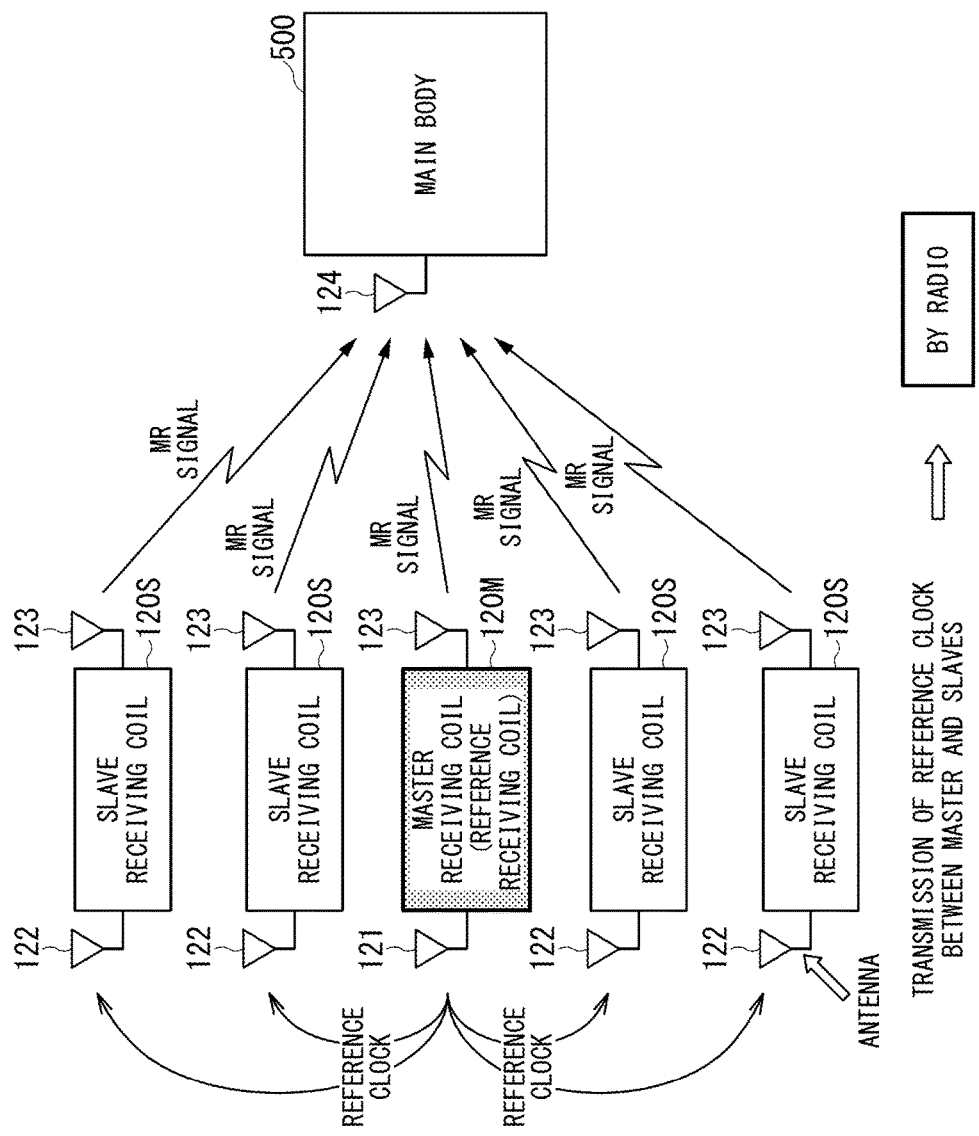
FIG. 3 is a schematic diagram showing an example of relationship between a master receiving coil, slave receiving coils, and a main body.

Each of the receiving coils 120 includes at least one coil element configured to detect a MR signal emitted from an object, an A/D converter configured to convert the MR signal detected by the coil element into a digital signal, a clock generation circuit configured to generate a reference clock for sampling, a radio transmission circuit configured to wirelessly transmit the digitized MR signal to a main body 500, and antennas 122 and 123 as shown in FIG. 3 to be described below.

The above-described main body 500 is an entire configuration of the MRI apparatus 1 excluding the receiving coils 120 and the whole body coil 12 (see FIG. 1).

FIG. 3 is a schematic diagram showing an example of relationship between the master receiving coil 120M, the slave receiving coils 120S, and the main body 500 and also showing main signals transmitted and received between them.

The difference between the master receiving coil 120M and each of the slave receiving coils 120S lies in how to use the reference clock for each A/D conversion. Each of the receiving coils 120 includes a built-in circuit for generating the reference clock for A/D conversion. However, if each of the receiving coils 120 independently uses its own reference clock generated by its built-in clock generation circuit for each A/D conversion, the reference clock for A/D conversion cannot be synchronized between the receiving coils 120.

For the above reason, while the receiving coils 120 selected as the master receiving coil 120M performs A/D conversion on MR signals by using the reference clock generated by its built-in clock generation circuit, the master receiving coil 120M also transmits this reference clock to each of the slave receiving coils 120S.

On the other hand, each of the slave receiving coils 120S synchronizes the reference clock generated by its built-in clock generation circuit with the reference clock received from the master receiving coil 120M.

Although transmission of the reference clock from the master receiving coil 120M to each of the slave receiving coils 120S may be wirelessly performed, it may be performed by wire. This is because distance between the master receiving coil 120M and each of the slave receiving coils 120S is comparatively small.

FIG. 3 shows an example in which transmission of the reference clock from the master receiving coil 120M to each of the slave receiving coils 120S is wirelessly performed. In this case, the reference clock is wirelessly transmitted from a transmission antenna 121 of the master receiving coil 120M to the reception antenna 122 of each of the slave receiving coils 120S.

The MR signals subjected to A/D conversion in the master receiving coil 120M and each of the slave receiving coils 120S are wirelessly transmitted to a reception antenna 124 of the main body 500 via the transmission antenna 123 of each of the master receiving coil 120M and the slave receiving coils 120S. Then, the MR signals received by the reception antenna 124 are converted into raw data, which are quadrature-detected I/Q digital signals of the baseband, by the receiving converter 32 (see FIG. 1). These raw data of the MR signals are transmitted to the console 400 via the sequence controller 34.

(2) Configuration of Master Receiving Coil and Slave Receiving Coil

Figure 4:
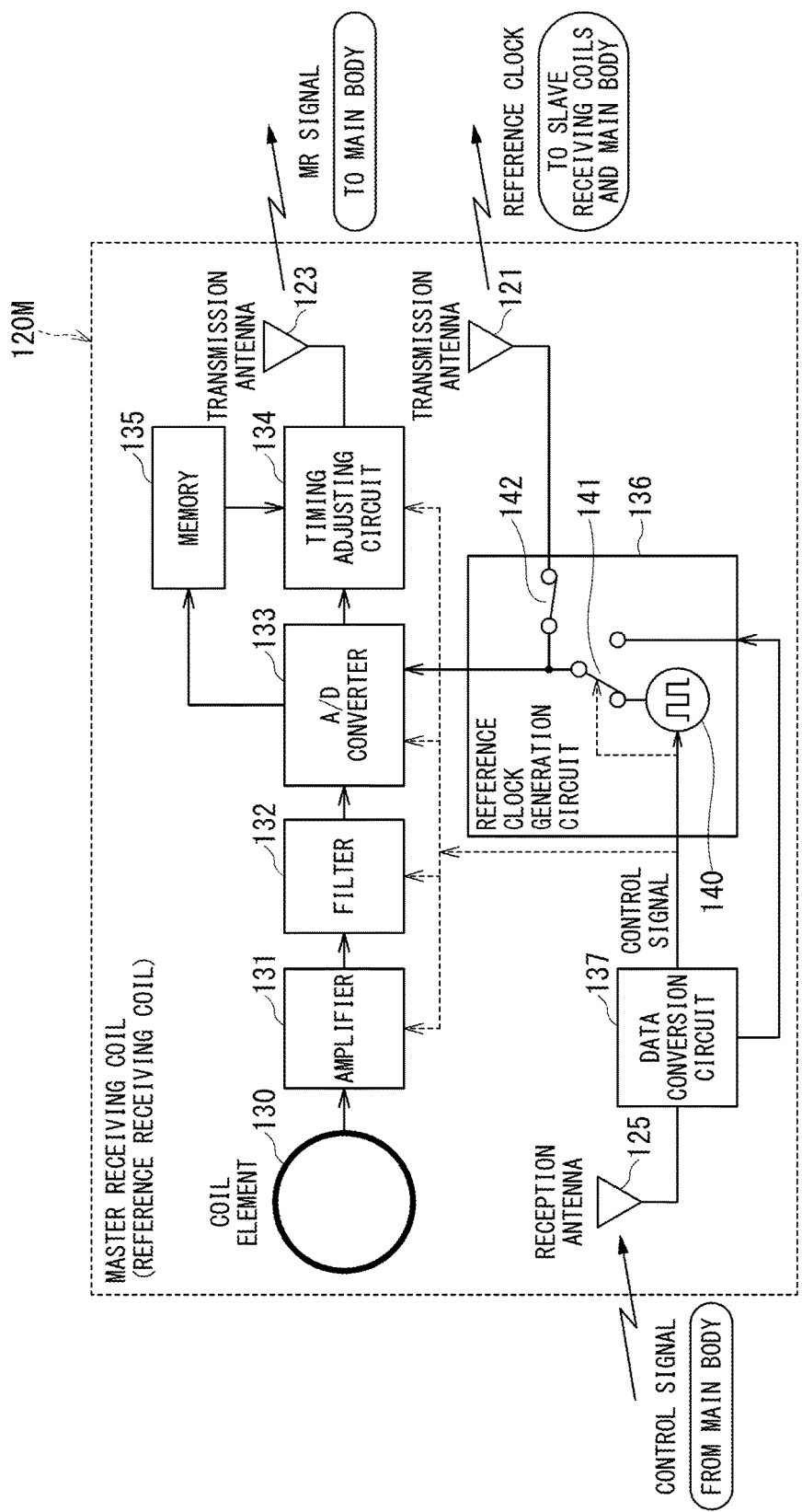
FIG. 4 is a schematic diagram showing an example of detailed configuration of the master receiving coil.
Figure 5:
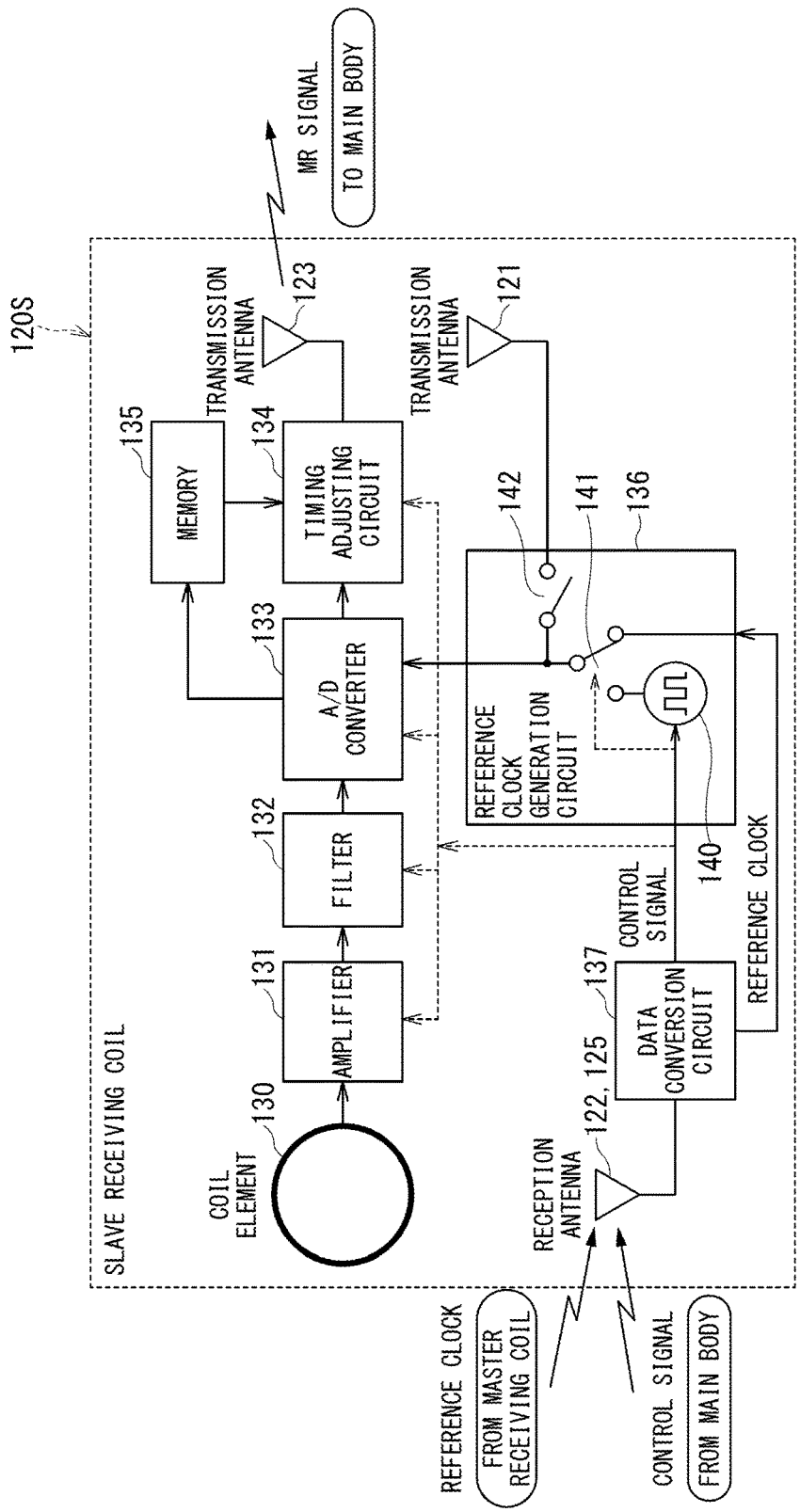
FIG. 5 is a schematic diagram showing an example of detailed configuration of each of the slave receiving coils.

FIG. 4 is a schematic diagram showing an example of detailed configuration of the master receiving coil 120M, and FIG. 5 is a schematic diagram showing an example of detailed configuration of each of the slave receiving coils 120S.

The master receiving coil 120M shown in FIG. 4 includes components such as an amplifier 131, a filter 132, an A/D converter 133, a timing adjusting circuit 134, a memory 135, a reference clock generation circuit 136, a data conversion circuit 137, the transmission antennas 121 and 123, a reception antenna 125, in addition to at least one coil element 130 configured to detect a MR signal emitted from an object.

The MR signal detected by the coil element 130 is amplified by the amplifier 131. Afterward, the frequency band of the amplified MR signals is limited to a predetermined frequency band by the filter 132, and then the MR signal subjected to the above band-limiting processing is sampled by the A/D converter 133 so as to be converted into a digital signal. The digitized MR signal is subjected to an appropriate timing adjustment processing by the timing adjusting circuit 134, then converted into radio signals, and then wirelessly transmitted from the transmission antenna 123 to the main body 500.

In addition, the master receiving coil 120M may be configured to temporarily store the digitized MR signal in the memory 135, read out the stored MR signal, and transmit the MR signal to the main body 500 at a predetermined timing. In this case, the master receiving coil 120M may be configured to add an ID (identification) number to each data set of the MR signal. Thereby, when wireless transmission of data of the MR signal partially fails, the master receiving coil 120M can identify the unsuccessfully transmitted data set of by the ID number and can retransmit the identified data set.

Further, the master receiving coil 120M may perform either (a) the processing of temporarily storing data of MR signals and transmitting the data of MR signals to the main body 500 at a predetermined timing or (b) the processing of adding the ID number to each data set of MR signals, identify and retransmit the unsuccessfully transmitted data set.

The reference clock generation circuit 136 includes a clock generator 140, a first switch 141 and a second switch 142. In the receiving coil 120 selected as the master receiving coil 120M, the first switch 141 is connected to the side of the clock generator 140 and the second switch 142 is switched into a "closed" state, as shown in FIG. 4.

Thus, the reference clock generated by the clock generator 140 is sent to the A/D converter 133 via the first switch 141, and is also sent to the transmission antenna 121 via the first switch 141 and the second switch 142. The wirelessly transmits this reference clock to each of the slave receiving coils 120S.

Incidentally, the MRI apparatus 1 may be configured so that the master receiving coil 120M wirelessly transmits the reference clock to the main body 500 via the transmission antenna 121.

Further, the master receiving coil 120M may be configured to include only one transmission antenna commonly used for transmission of data of MR signals and transmission of the reference clock, by omitting one of the transmission antennas 121 and 123 as an example.

The reception antenna 125 receives various types of control signals wirelessly transmitted from the main body 500. The data conversion circuit 137 converts each of the control signals into an appropriate format, and sends the converted control signals to respective components in the master receiving coil 120M.

The control signals transmitted from the main body 500 are low-speed signals, as compared with the MR signal and the reference clock. The control signals transmitted from the main body 500 include, for example, data indicative of the center frequency of transmission and reception and/or deviation from the center frequency called delta f, a synchronization signal used for electrocardiographic synchronization imaging, a timing signal indicative of a start timing of sampling, data indicative of sampling interval and/or sampling number, data designating a reception gain of each amplifier 131, and data designating a reception band of the filter 132.

In addition, the control signals transmitted from the main body 500 include a master/slave designation signal in which each of the receiving coils 120 is distinguished by its identification information and is designated as either the master receiving coil 120M or the slave receiving coil 120S. In one of the receiving coils 120 which is designated as a master by the master/slave designation signal, the first switch 141 is connected to the side of the clock generator 140 and the second switch 142 is switched into a closed state as shown in FIG. 4.

FIG. 5 is a schematic diagram showing an example of detailed configuration of each of the slave receiving coils 120S. The hardware structure of each of the slave receiving coils 120S is basically the same as that of the master receiving coil 120M. However, the difference between both s in that each of the slave receiving coils 120S synchronizes the reference clock used for the A/D converter 133 with the reference clock transmitted from the master receiving coil 120M.

Thus, each of the slave receiving coils 120S includes the reception antenna 122 for wirelessly receiving the reference clock from the master receiving coil 120M. Incidentally, each of the slave receiving coils 120S may be configured to include only one reception antenna commonly used for reception of the reference clock and control signals as shown in FIG. 5, by omitting one of the reception antennas 122 and 125 as an example. The reference clock received by the reception antenna 122 is inputted to the reference clock generation circuit 136 via the data conversion circuit 137.

The easiest method of synchronizing the reference clock of each of the slave receiving coils 120S with the reference clock of the master receiving coil 12014 is to switch the reference clock (i.e., the output of the clock generator 140) of each of the slave receiving coils 120S into the reference clock received from the master receiving coil 120M as shown in FIG. 5. The control signal for the switching operation is the above-described master/slave designation signal.

In each of the receiving coils 120 designated as a slave by the master/slave designation signal, i.e., in each slave receiving coil 120S, the first switch 141 and the second switch 142 are switched as shown in FIG. 5. In other words, the first switch 141 is separated from the side of the clock generator 140, and the received reference clock of the master receiving coil 120M is supplied to the A/D converter 133. Meanwhile, the second switch 142 is switched into an "opened" state, and thus, the reference clock is not transmitted from the transmission antenna 121.

Note that a method of synchronizing the reference clock of each of the slave receiving coils 120S with the reference clock of the master receiving coil 12014 is not limited to the above-described switching method. For example, the reference clock generation circuit 136 may be configured as an oscillator of PLL (Phase-Locked Loop) type. For example, the above-described idea may be configured as follows. Inside the master receiving coil 120M, a reference frequency is internally generated, the reference clock synchronized with this reference frequency is generated using the PLL oscillator, and this reference clock is supplied to the A/D converter 133. On the other hand, inside each of the slave receiving coils 120S, a reference clock synchronized with the frequency of the reference clock received from the master receiving coil 120M is generated using the PLL oscillator and supplied to the A/D converter 133.

Other than that, various modifications are possible as to configuration of the master receiving coil 120M and the slave receiving coils 120S.

For example, instead of wirelessly transmitting the MR signal from each of the slave receiving coils 120S to the main body 500, the master receiving coil 120M may be configured to collectively transmit all MR signals to the main body 500. Specifically, respective MR signals received by the slave receiving coils 120S may be collected by wire to the master receiving coil 120M, for example, and may be temporarily stored in an appropriate memory inside the master receiving coil 120M. Afterward, the master receiving coil 120M may collectively transmit all the MR signals received by each of the slave receiving coils 120S and the MR signals received by the master receiving coil 120M to the main body 500.

As another example, the master receiving coil 120M may be configured to command each of the slave receiving coils 120S to transmit MR signals to the main body 500 at the timing determined by the master receiving coil 120M so that the MR signals received by the respective receiving coils 120M and 120S are transmitted to the main body 500 in a time-division manner.

In the configuration of the above-described embodiment, the reference clock is generated inside the master receiving coil 120M. Alternatively the main body 500 may be configured to generate the reference clock and to wirelessly transmit this reference clock to the master receiving coil 120M. In this case, the master receiving coil 120M may be configured to be capable of switching between the reference clock generated inside and the reference clock wirelessly transmitted from the main body 500.

(3) Method of Determining Master Receiving Coil

As mentioned above, the master receiving coil 120M is determined by selecting one from the plural receiving coils 120. Hereinafter, methods of determining the master receiving coil 120M will be explained.

FIG. 6 is a functional block diagram showing an example of configuration relevant to determination of the master receiving coil 120M. Functions relevant to determination of the master receiving coil 120M are implemented by the processing circuitry 40 of the main body 500. Specifically, the processing circuitry 40 implements a coil position determination function 511, a coil type determination function 512, a signal intensity determination function 513, and a master/slave determination function 514. For example, the processing circuitry 40 is equipped with a processor and this processor implements the above described functions by executing predetermined programs stored in the memory circuitry 41. Alternatively or additionally, the programs executed by the processor of the processing circuitry 40 for implementing each of the above-described functions may be directly stored in the circuit of the processor.

Each of the receiving coils 120 arranged on the table 21 transmits its identification information to the main body 500, via the same channel as that of the MR signals wirelessly transmitted from each of the receiving coils 120. The coil position determination function 511 of the processing circuitry 40 determines the position of each of the receiving coils 120 arranged on the table 21 by using the identification information. In addition, the coil type determination function 512 determines a type of each of the receiving coils 120 arranged on the table 21 by using the identification information.

The signal intensity determination function 513 determines intensity of MR signals received by the receiving coils 120. Calibration scans are generally performed before a main scan, in order to perform various types of calibration such as adjustment of a reception gain. The signal intensity determination function 513 can determine reception intensity of each of the receiving coils 120 for receiving MR signals, based on the MR signals obtained in one of the calibration scans.

In addition, the processing circuitry 40 can acquire positional information of a ROI (region of interest) of an object and positional information of imaging regions such as a slice position and a slab position, based on imaging conditions having been set by a user.

The master/slave determination function 514 determines the master receiving coil 120M by selecting one of the plural receiving coils 120, based on the above-described information including positions of the respective receiving coils 120, a type of each of the receiving coils 120, intensity of MR signals received by each of the receiving coils 120, positional information of a ROI and imaging regions, and a preliminarily determined LUT (look-up table).

Hereinafter, methods of determining the master receiving coil 120M will be more specifically explained in order by reference to the functional block diagram of FIG. 6, and FIG. 7 to FIG. 14.

(3-1) First Embodiment

Figure 7A:
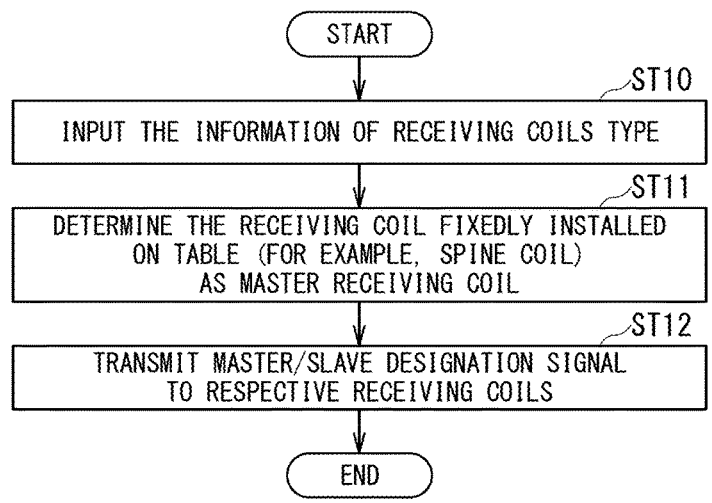
FIG. 7A is a flowchart showing an example of a method of determining the master receiving coil in the first embodiment.
Figure 7B:
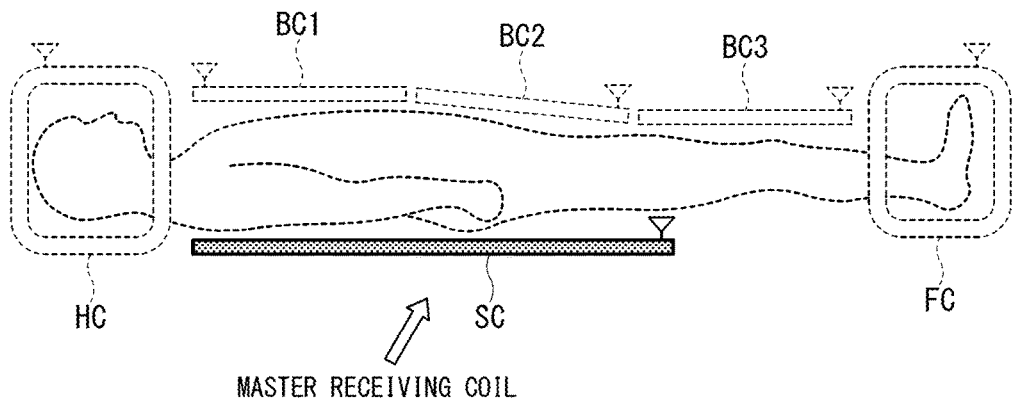
FIG. 7B is a receiving coil arrangement diagram showing an example of a method of determining the master receiving coil in the first embodiment.

FIG. 7A is a flowchart showing an example of a method of determining the master receiving coil 120M in the first embodiment. FIG. 7B is a receiving coil arrangement diagram showing an example of a method of determining the master receiving coil 120M in the first embodiment.

In the first embodiment, the master receiving coil 120M is determined by selecting one from the receiving coils 120 each of which is installed on the table 21 as a fixed type. Specifically, as shown in FIG. 6 and FIG. 7A, the coil type determination function 512 of the processing circuitry 40 outputs information on each type of the receiving coils 120 which are currently set on the table 21, to the master/slave determination function 514 in the step ST10.

Next, in the step ST11, the master/slave determination function 514 determines the receiving coil 120 which is fixedly installed on the table 21 as the master receiving coil 12014, based on the inputted information. For example, the spine coil SC is fixedly installed on the table 21. In other word, the spine coil may often be set on the table 21 all the time regardless of imaging conditions such as an imaging position. By contrast, the body coils BC1, BC2, and BC3 may be attached to or detached from the object depending on imaging conditions such as the imaging position. In such a case, the spine coil SC is determined as the master receiving coil 120M in the first embodiment.

Afterward, in the step ST12, the master/slave determination function 514 of the processing circuitry 40 transmits the master/slave designation signal by which the spine coil SC is designated as the master receiving coil 120M and all the other receiving coils 120 are designated as the slave receiving coils 120S, to the respective the receiving coils 120.

Incidentally, as the type of the receiving coils 120 to be fixedly installed on the table 21, the head coil HC is also included in addition to the above spine coil Sc.

(3-2) Second Embodiment

Figure 8A:
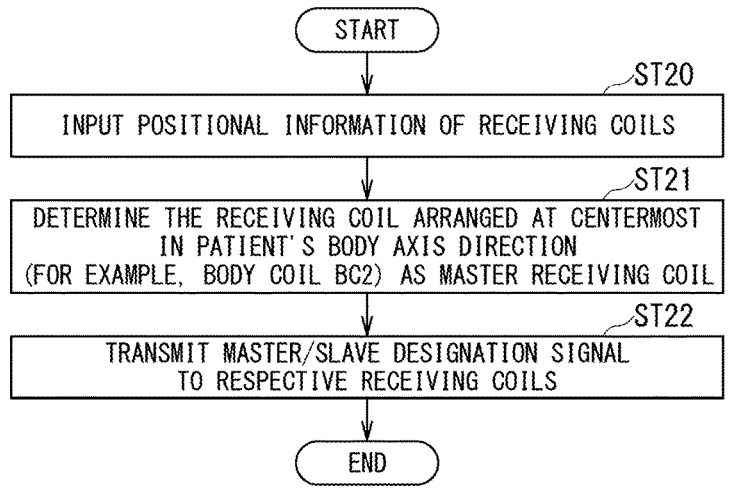
FIG. 8A is a flowchart showing an example of a method of determining the master receiving coil in the second embodiment.
Figure 8B:
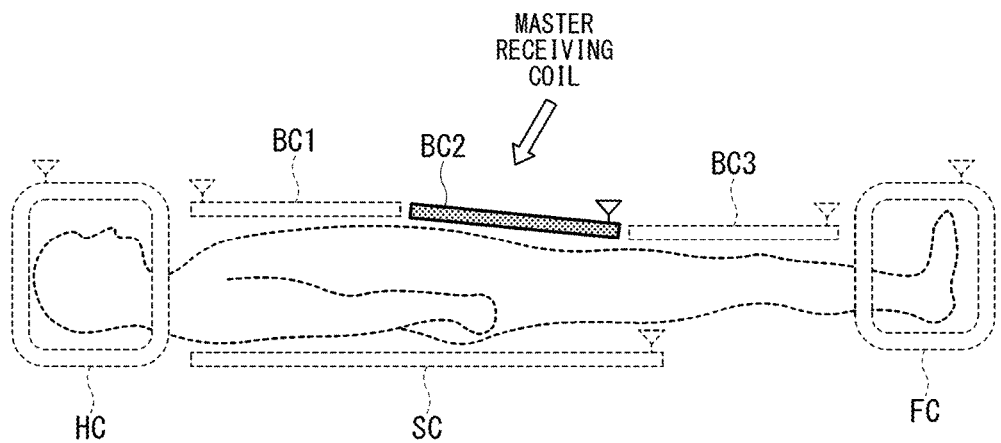
FIG. 8B is a receiving coil arrangement diagram showing an example of a method of determining the master receiving coil in the second embodiment.

FIG. 8A is a flowchart showing an example of a method of determining the master receiving coil 120M in the second embodiment. FIG. 8B is a receiving coil arrangement diagram showing an example of a method of determining the master receiving coil 120M in the second embodiment.

In the second embodiment, the coil position determination function 511 of the processing circuitry 40 outputs the positional information of the respective receiving coils 120 which are currently set on the table 21, to the master/slave determination function 514 in the step ST20 as shown in FIG. 6 and FIG. 8A.

Next, in the step ST21, the master/slave determination function 514 determines the receiving coil 120 substantially arranged at the midpoint (i.e., centermost) in the patient's body axis direction (i.e., in the head-foot direction) out of all the receiving coils 120, as the master receiving coil 120M. This determination is performed based on the inputted positional information. In the example shown in FIG. 8B, the body coil BC2 is arranged at the centermost in the body axis direction. Therefore, the body coil BC2 is determined as the master receiving coil 120M.

Afterward, in the step ST22, the master/slave determination function 514 transmits the master/slave designation signal to the respective receiving coils 120.

Since the master receiving coil 120M determined in the algorithm of the second embodiment is located at the centermost in the body axis direction, the interval between the master receiving coil 120M and the most distant slave receiving coil 120S can be minimized. In other words, the maximum transmission distance from the master receiving coil 120M to each of the slave receiving coils 120S can be minimized. As a result, degradation of transmission quality of the reference clock transmitted from the master receiving coil 120M to each of the slave receiving coils 120S can be minimized. For example, the transmission delay time from the master receiving coil 120M to the most distant slave receiving coils 120S can be minimized. Thereby, timings of the rising edge and falling edge of the reference clock can be satisfactorily synchronized between the master receiving coil 120M and the respective slave receiving coils 120S.

(3-3) Third Embodiment

Figure 9A:
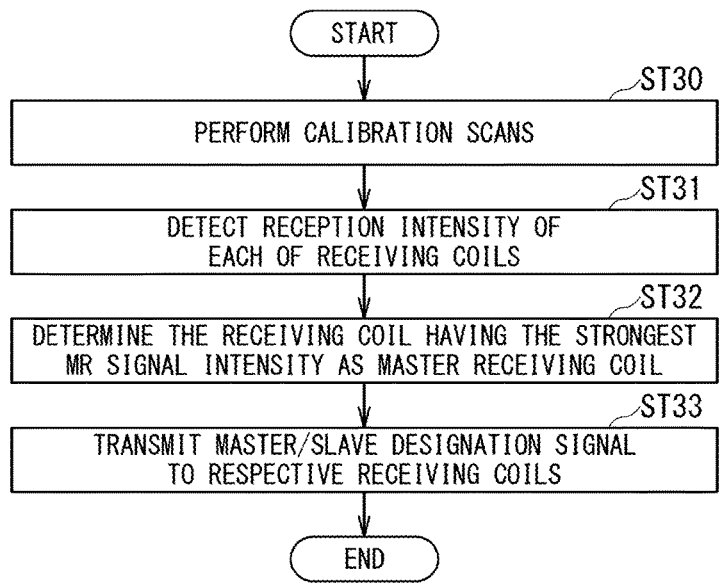
FIG. 9A is a flowchart showing an example of a method of determining the master receiving coil in the third embodiment.
Figure 9B:
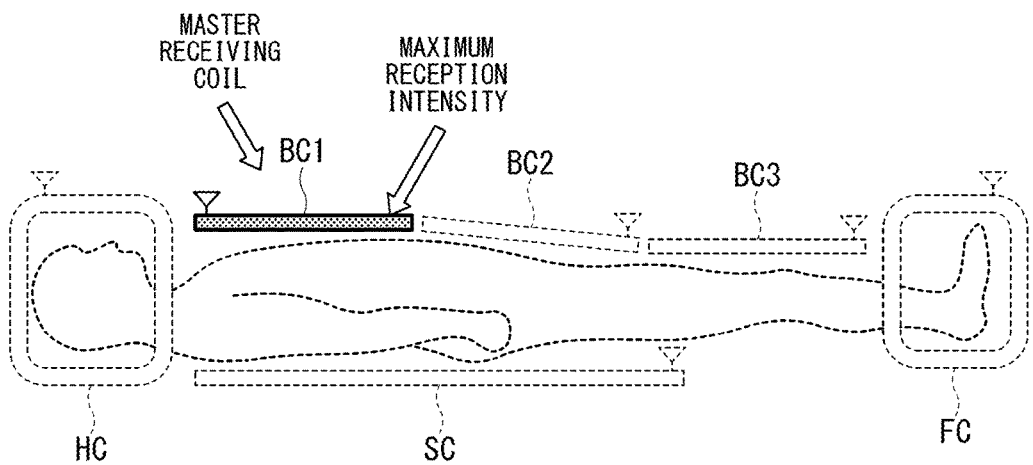
FIG. 9B is a receiving coil arrangement diagram showing an example of a method of determining the master receiving coil in the third embodiment.

FIG. 9A is a flowchart showing an example of a method of determining the master receiving coil 120M in the third embodiment. FIG. 9B is a receiving coil arrangement diagram showing an example of a method of determining the master receiving coil 120M in the third embodiment.

In the third embodiment, the processing circuitry 40 controls the respective components of the MRI apparatus 1 so that the MRI apparatus 1 performs the above-described calibration scan in the step ST30 (see FIG. 9A and FIG. 1).

Next, in the step ST31, the signal intensity determination function 513 of the processing circuitry 40 detects reception intensity of MR signals obtained by the calibration scans for each of the receiving coils 120.

Next, in the step ST32, the master/slave determination function 514 determines the receiving coil 120 showing the strongest MR signal intensity as the master receiving coil 120M. For example, when the MR signal intensity of the body coil BC1 is the strongest, the master/slave determination function 514 determines the body coil BC1 as the master receiving coil 120M.

Afterward, in the step ST33, the master/slave determination function 514 transmits the master/slave designation signal to the respective receiving coils 120.

When a combined image is generated by using MR signals obtained from plural receiving coils 120, MR signals received by the receiving coil 120 with stronger MR signal intensity have larger influence on the combined image than MR signals received by the receiving coil 120 with smaller MR signal intensity. In the third embodiment, one of the receiving coils 120 which has the largest influence on an combined image is determined as the master receiving coil 120M.

Even if the sampling timing of each of the slave receiving coils 120S is shifted to some extent with respect to the sampling timing of the master receiving coil 120M due to synchronization shift of the reference clock between the master receiving coil 120M and each of the slave receiving coils 120S, degradation of quality of the combined image can be minimized according to the above-described determination method. This is because MR signals received by the slave receiving coils 120S have smaller contribution to the combined image than MR signals received by the master receiving coil 120M.

(3-4) Fourth Embodiment

Figure 10A:
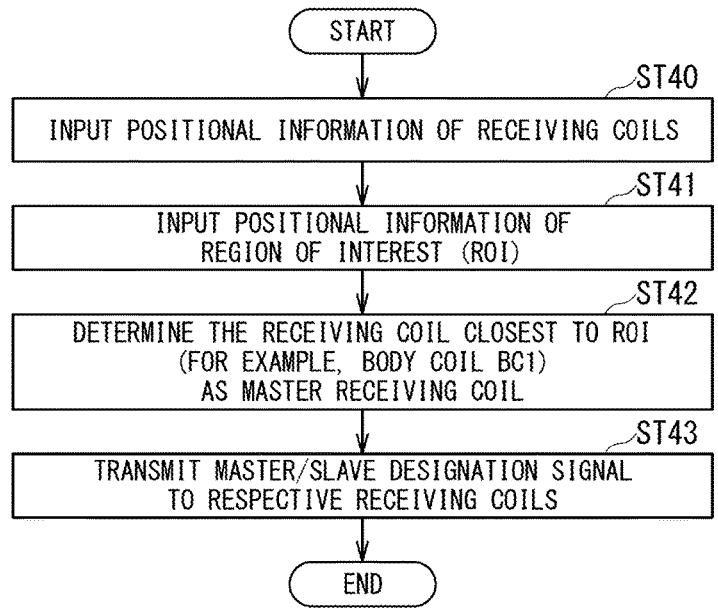
FIG. 10A is a flowchart showing an example of a method of determining the master receiving coil in the fourth embodiment.
Figure 10B:
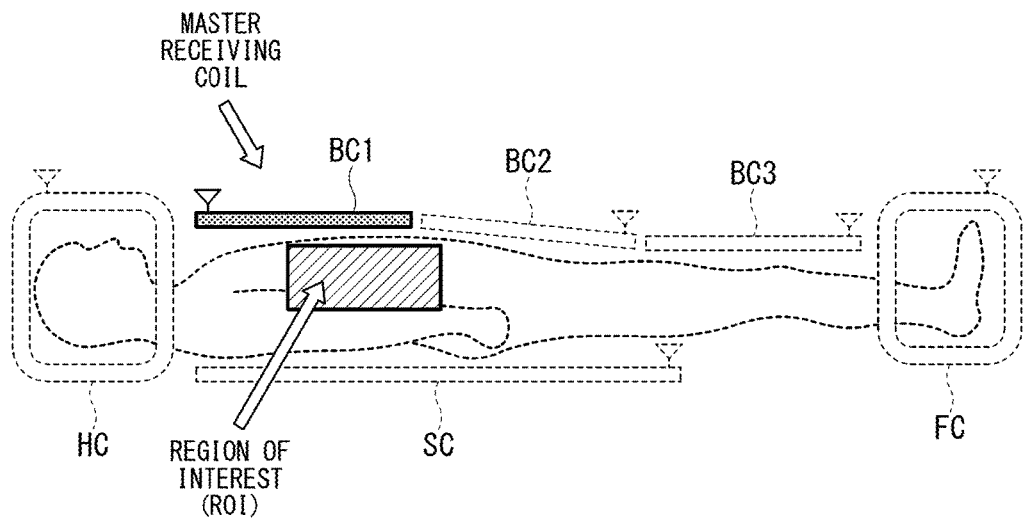
FIG. 10B is a receiving coil arrangement diagram showing an example of a method of determining the master receiving coil in the fourth embodiment.

FIG. 10A is a flowchart showing an example of a method of determining the master receiving coil 120M in the fourth embodiment. FIG. 10B is a receiving coil arrangement diagram showing an example of a method of determining the master receiving coil 120M in the fourth embodiment. The determination method of the fourth embodiment is similar to the third embodiment, because one of the receiving coils 120 having stronger reception intensity is determined as the master receiving coil 120M.

In the step ST40 of the fourth embodiment as shown in FIG. 10A, the positional information of the respective receiving coils 120 is inputted to the master/slave determination function 514 in a similar manner as described above.

Further, in the next step ST41, the master/slave determination function 514 acquires the positional information of the ROI based on the contents inputted by a user via the input device 42, for example.

When the ROI is imaged by using the plural receiving coils 120, it is generally considered that the receiving coil 120 closest to the ROI receives the MR signal having the strongest intensity. For this reason, the receiving coils 120 closest to the ROI is determined as the master receiving coil 120M in the step ST42 in the fourth embodiment. In the example of FIG. 10B, the body coil BC1 is determined as the master receiving coil 120M.

Afterward, in the step ST43, the master/slave determination function 514 transmits the master/slave designation signal to each of the receiving coils 120. Also in the fourth embodiment, the receiving coil 120 having larger contribution to a combined image is determined as the master receiving coil 120M and all the other receiving coils 120 having smaller contribution to a combined image are determined as the slave receiving coils 120S. Thereby, satisfactory image quality of the combined image can be kept high in the fourth embodiment.

(3-5) Fifth Embodiment

Figure 11A:
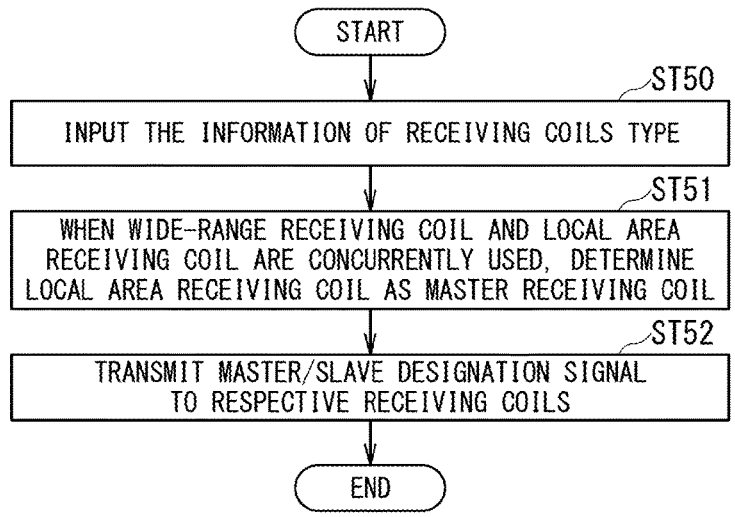
FIG. 11A is a flowchart showing an example of a method of determining the master receiving coil in the fifth embodiment.
Figure 11B:
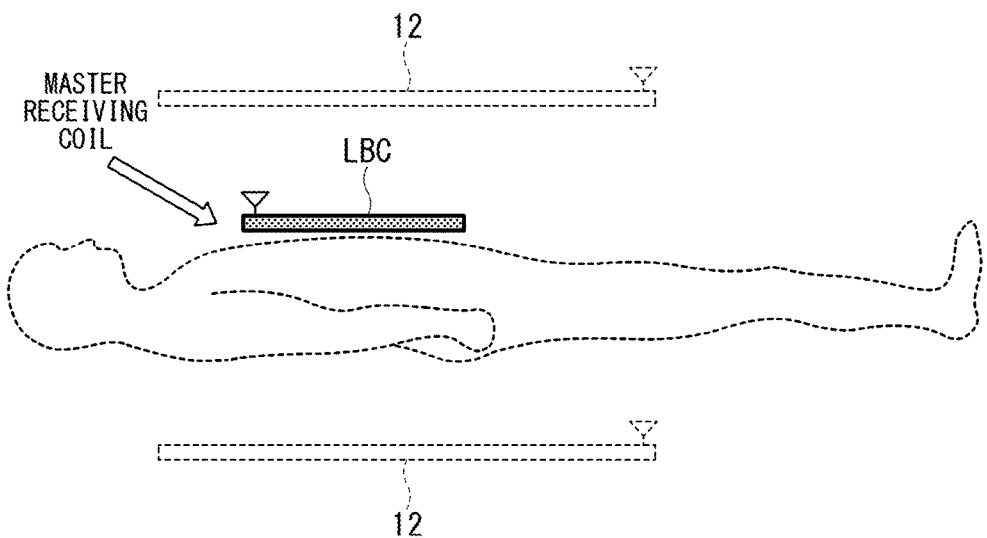
FIG. 11B is a receiving coil arrangement diagram showing an example of a method of determining the master receiving coil in the fifth embodiment.

FIG. 11A is a flowchart showing an example of a method of determining the master receiving coil 120M in the fifth embodiment. FIG. 11B is a receiving coil arrangement diagram showing an example of a method of determining the master receiving coil 120M in the fifth embodiment. The determination method of the fifth embodiment is also similar to the above-described third and fourth embodiments, because one of the receiving coils 120 having stronger reception intensity is determined as the master receiving coil 120M.

When imaging of an object, a wide-range receiving coil capable of receiving MR signals from a comparatively wide range and a local receiving coil configured to receive MR signals from a narrow region are sometimes concurrently used. In such a case, it can be regarded that the local receiving coil has stronger reception intensity than the wide-range receiving coil.

FIG. 11B shows an example in which the whole body c 12 as a wide-range receiving coil and the body coil LBC as a local area receiving coil are concurrently used.

First, in the step ST50 of FIG. 11A, the information on the type of the receiving coils 120 is inputted to the master/slave determination function 514 of the processing circuitry 40 in a similar manner as described above.

Next, when a wide-range receiving coil and a local area receiving coil are concurrently used, the master/slave determination function 514 determines the local area receiving coil as the master receiving coil 120M in the step ST51, and then transmits the master/slave designation signal to each of the receiving coils 120 in the step ST52.

Figure 12A:
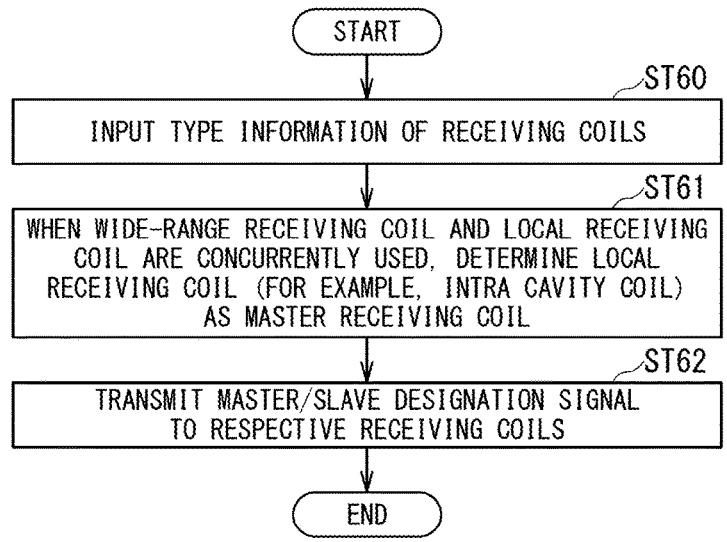
FIG. 12A is a flowchart showing an example in which a body coil and a spine coil as wide-range receiving coils and an intra cavity coil as a local receiving coil are concurrently used.
Figure 12B:
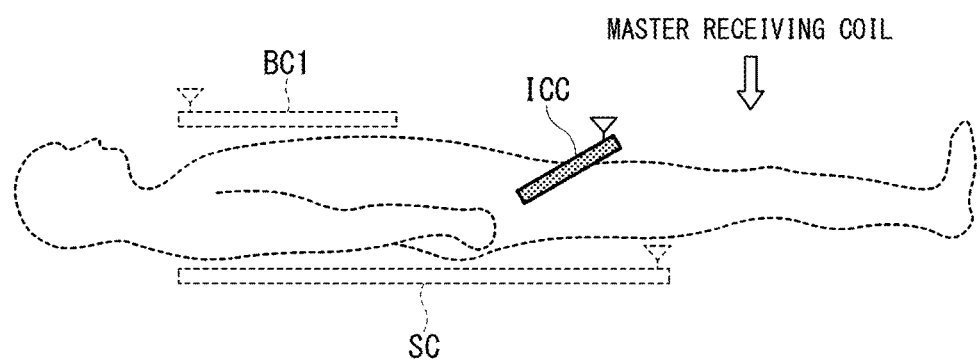
FIG. 12B is a receiving coil arrangement diagram of an example of FIG. 12A in which the body coil, the spine coil, and the intra cavity coil are concurrently used.

FIG. 12A is a flowchart showing an example in which the body coil BC1 and the spine coil SC as wide-range receiving coils, and an intra cavity coil ICC as a local receiving coil are concurrently used. FIG. 12B is a receiving coil arrangement diagram of an example in which the body coil BC1, the spine coil SC, and the intra cavity coil are concurrently used. The intra cavity coil ICC is a pencil type local coil inserted into the rectum in the case of diagnosing the prostate gland as an example.

First, in the step ST60, the type information of the receiving coils 120 is inputted to the master/slave determination function 514 of the processing circuitry 40 in a similar manner as described above. Next, when a wide-range receiving coil and a local receiving coil are concurrently used, the master/slave determination function 514 determines the local receiving coil (e.g., the intra cavity coil ICC) as the master receiving coil 120M in the step ST61, and then transmits the master/slave designation signal to each of the receiving coils 120 in the step ST62.

(3-6) Sixth Embodiment

The main point of the sixth embodiment is as follows. When imaging of one imaging region and switching the imaging region to the next region are sequentially repeated to image plural imaging regions, the receiving coil 120 closest to the updated imaging region is newly selected as the master receiving coil 120M, according to movement of the imaging region.

Figure 13A:
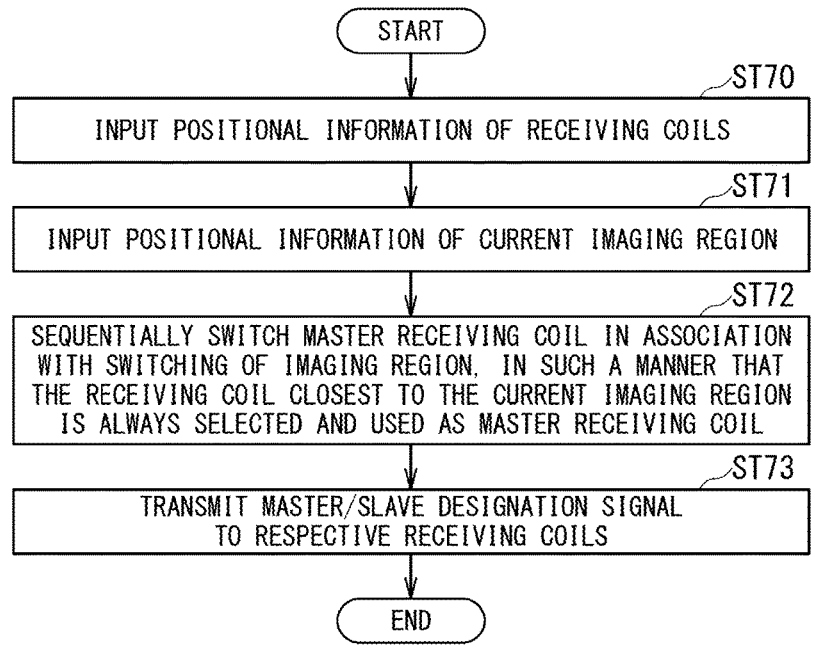
FIG. 13A is a flowchart showing an example of a method of determining the master receiving coil in the sixth embodiment.
Figure 13B:
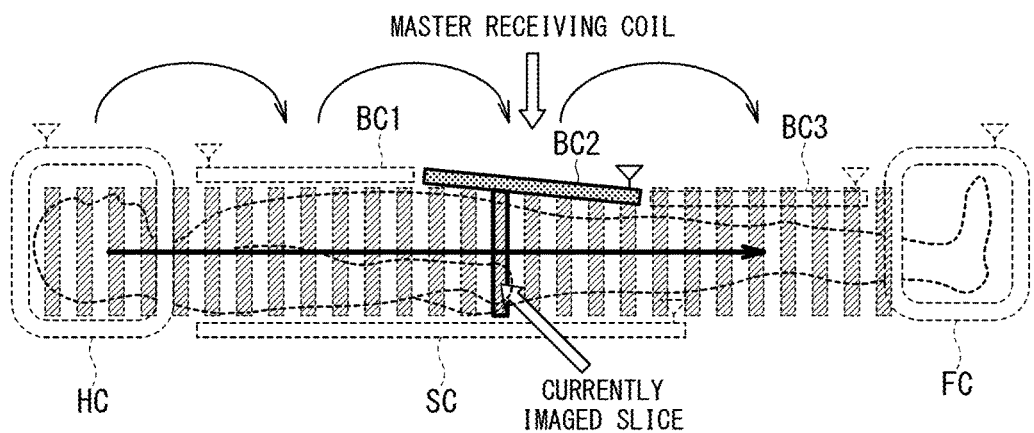
FIG. 13B is a receiving coil arrangement diagram showing an example of a method of determining the master receiving coil in the sixth embodiment.

FIG. 13A is a flowchart showing an example of a method of determining the master receiving coil 120M in the sixth embodiment. FIG. 13B is a receiving coil arrangement diagram showing an example of a method of determining the master receiving coil 120M in the sixth embodiment. In the case of imaging the whole body of an object, for example, there is an imaging method in which an imaging region such as a slice and/or a slab of an axial plane is sequentially set from the head to the foot by moving the table 21 and imaging is sequentially performed for each imaging region as shown in FIG. 13B.

Alternatively, there is an imaging method in which a comparatively wide range of an object is imaged by sequentially switching a slice and/or a slab while fixing the position of the table 21. The above-described comparatively wide range means a range covered by the receiving coils 120 attached to the object and/or installed on the table 21. The method of determining the master receiving coil 120M in the sixth embodiment is applicable to the above-described imaging methods.

First, in the step ST70 of FIG. 13A, the positional information of the respective receiving coils 120 arranged around the object is inputted to the master/slave determination function 514 of the processing circuitry 40 in a similar manner as described above. After imaging is started, the positional information of the current imaging region is sequentially inputted to the master/slave determination function 514 in the step ST71, while an imaging region such as a slice and/or a slab is sequentially switched to the next one. In other words, the positional information of each of the receiving coils 120 is updated.

Then, in the step ST72, the master/slave determination function 514 sequentially switches the master receiving coil 120M, in such a manner that the receiving coil 120 closest to the currently imaged imaging region (e.g., a slice and/or a slab) is newly selected as the master receiving coil 120M, each time the imaging region is switched to the next one.

By the above processing of switching the master receiving coil 120M, the master receiving coil 120M is switched from one receiving coil 120 to its adjacent receiving coil 120. Each time the master receiving coil 120M is switched, the master/slave determination function 514 transmits the master/slave designation signal to each of the receiving coils 120 as shown in the step ST73.

According to the sixth embodiment, even in the case of imaging a wide range of an object sequentially, the master receiving coil 120M can be appropriately selected and switched according to switching of an imaging region. In addition, the receiving coil 120 closest to the current imaging region is always determined as the master receiving coil 120M each time of switching the imaging region. Thus, the receiving coil 120 having the largest reception intensity can be always selected as the master receiving coil 120M regardless of switching of an imaging region.

(3-7) Seventh Embodiment

Figure 14A:
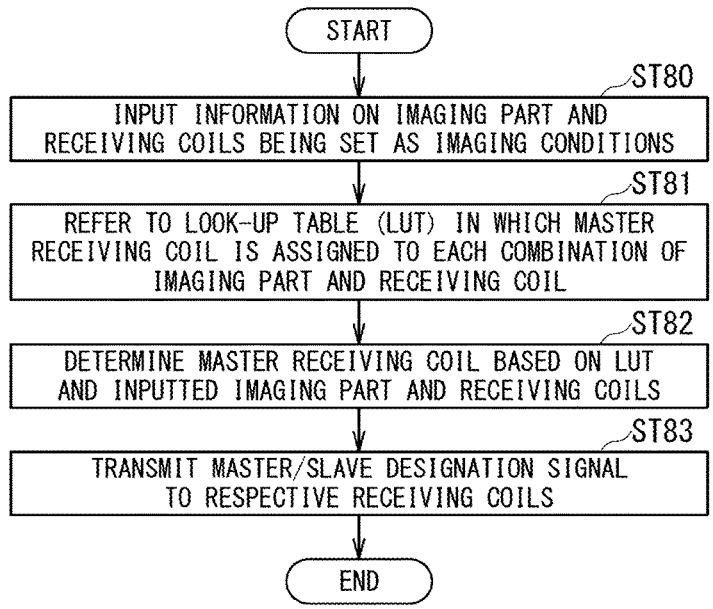
FIG. 14A is a flowchart showing an example of a method of determining the master receiving coil in the seventh embodiment.
Figure 14B:
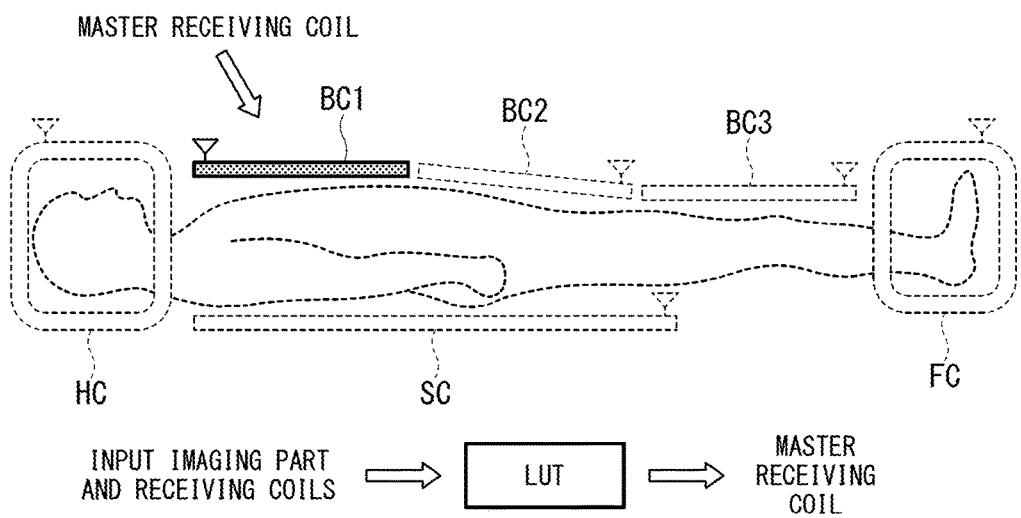
FIG. 14B is a receiving coil arrangement diagram showing an example of a method of determining the master receiving coil in the seventh embodiment.

FIG. 14A is a flowchart showing an example of a method of determining the master receiving coil 120M in the seventh embodiment. FIG. 14B is a receiving coil arrangement diagram showing an example of a method of determining the master receiving coil 120M in the seventh embodiment. In the seventh embodiment, the processing circuitry 40 determines the master receiving coil 120M by reference to a look-up table (LUT).

When imaging of an object is planned, an imaging part and a type of receiving coil are designated as imaging conditions in many cases. A receiving coil A and a receiving coil B may be set for a specific imaging part A in some cases, while the receiving coil A and a receiving coil C may be set for the same imaging part A in other cases. In other words, there are many combination patterns of imaging parts and receiving coils.

For the above reason, one master receiving coil 120M is preliminarily assigned to each of possible combination patterns of an imaging part and receiving coil(s) in the look-up table. Although a case where the look-up table is stored in the memory circuitry 41 will be explained as an example here, the look-up table may be stored in the processing circuitry 40.

First, in the step ST80 of FIG. 14A, information on an imaging part and receiving coils having been set as imaging conditions are inputted to the processing circuitry 40 via the input device 42 shown in FIG. 1.

Next, in the step ST81, the master/slave determination function 514 of the processing circuitry 40 refers to the above-described look-up table in which the master receiving coil 120M and each of combination patterns of an imaging part and receiving coil(s) are associated with each other.

Next, in the step ST82, the master/slave determination function 514 determines the master receiving coil 120M based on the imaging part and receiving coil(s) inputted in the step ST80 and the look-up table.

Afterward, in the step ST83, the master/slave determination function 514 transmits the master/slave designation signal to each of the receiving coils 120.

(4) Other Embodiments

The embodiment shown in FIG. 3 is explained under the premise that transmission of the reference clock between the master receiving coil 120M and each of the slave receiving coils 120S is wirelessly performed.

However, the distance between the master receiving coil 120M and each of the slave receiving coils 120S is comparatively short and the transmission of the reference clock is not necessarily needed to be wirelessly performed.

Figure 15:
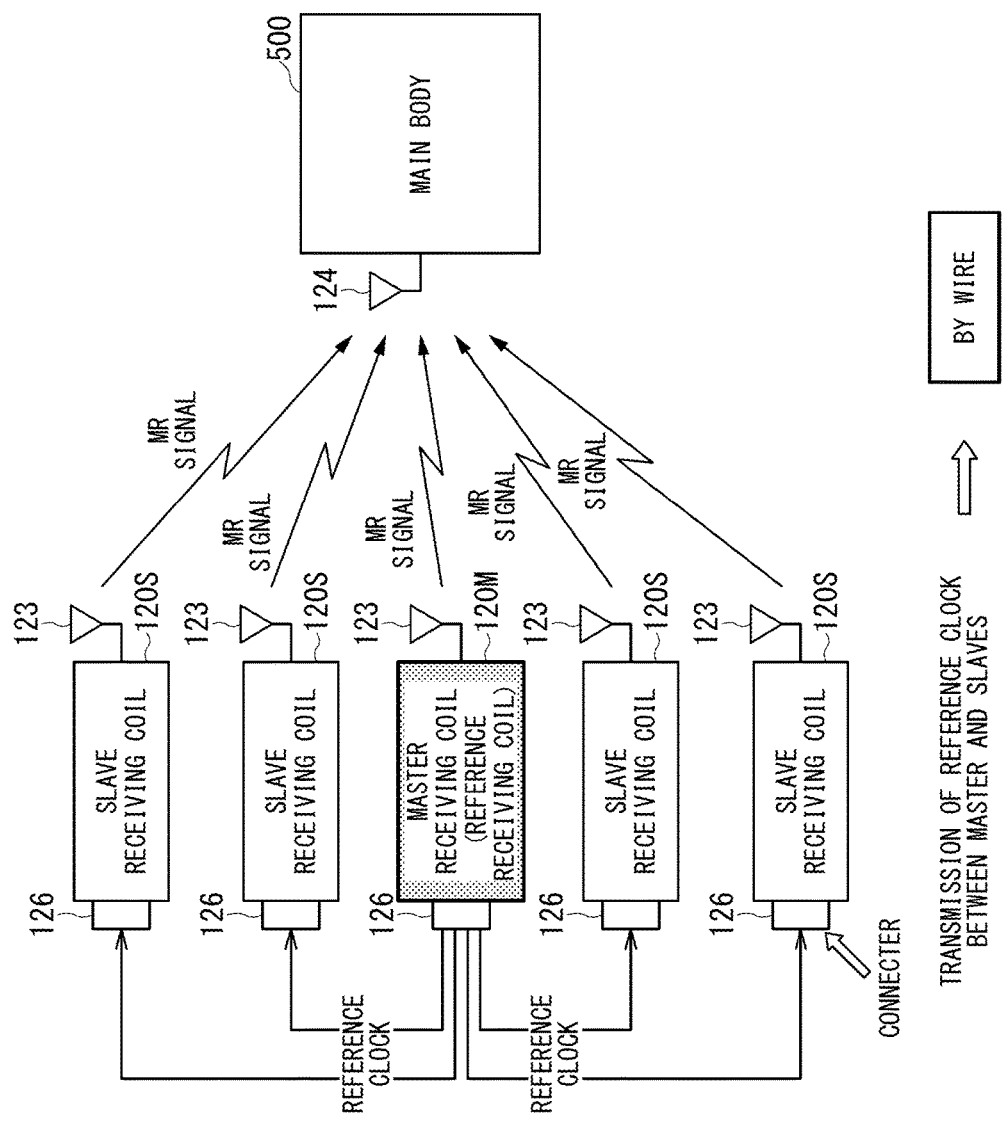
FIG. 15 is schematic block diagram explaining an embodiment in which the reference clock is transmitted by wire.

As shown in FIG. 15 as an example, the transmission of the reference clock between the master receiving coil 120M and each of the slave receiving coils 120S may be performed by wire via a connector 126.

Figure 16:
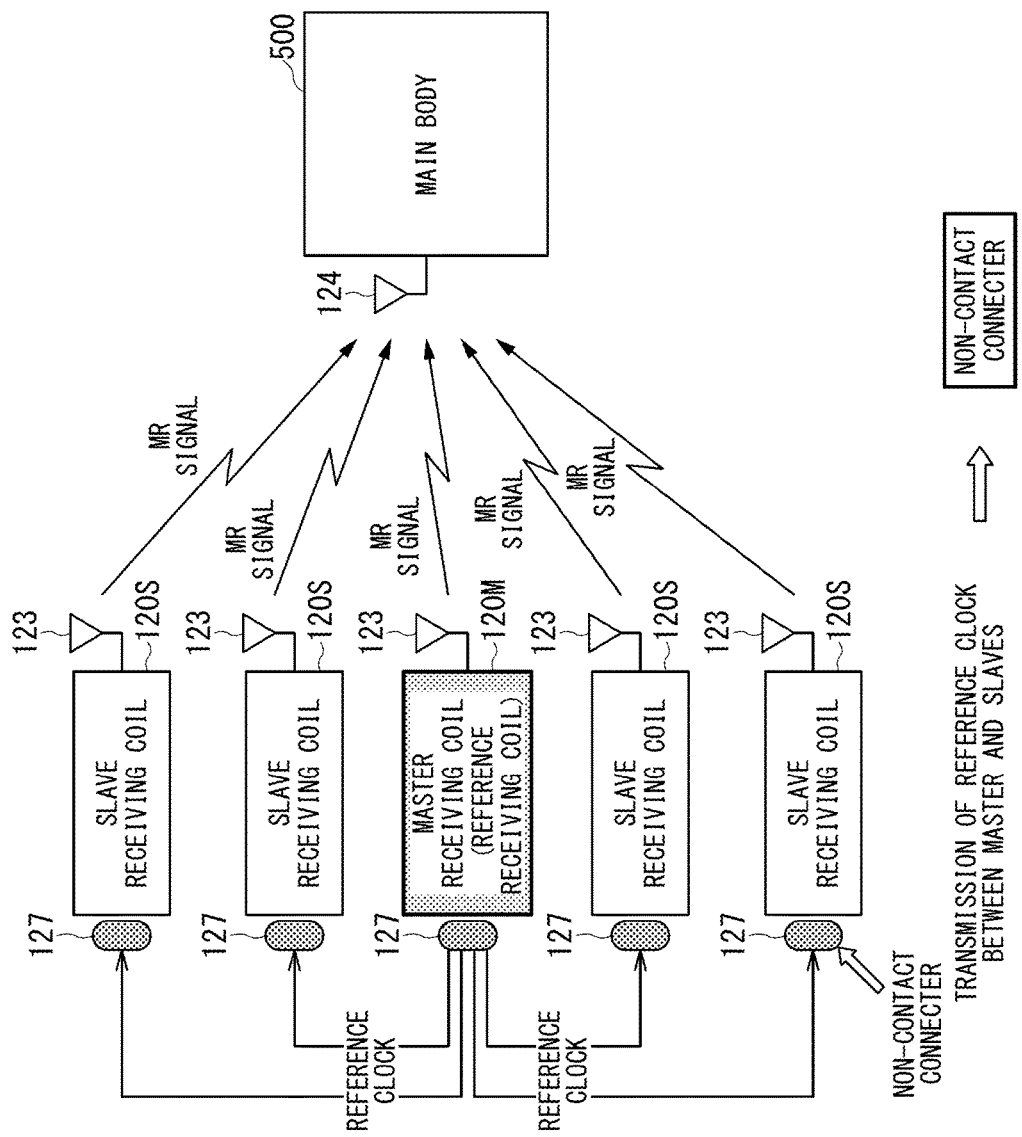
FIG. 16 is schematic block diagram explaining an embodiment in which the reference clock is transmitted using a non-contact connector.

In addition, as shown in FIG. 16, the transmission of the reference clock between the master receiving coil 120M and each of the slave receiving coils 120S may be performed via a non-contact connector 127.

As mentioned above, the MRI apparatus 1 of each of the above embodiments and their modifications can determine one master receiving coil 120M out of plural built-in clock type receiving coils 120 and can synchronize the reference clock of each of the slave receiving coils 120S with the reference clock of the master receiving coil 120M.

Incidentally, the term "processor" used for explaining the processing circuitry 40 means, for instance, a circuit such as a CPU (Central Processing Unit), a GPU (Graphics Processing Unit), an ASIC (Application Specific Integrated Circuit), a programmable logic device including an SPLD (Simple Programmable Logic Device) and a CPLD (Complex Programmable Logic Device) as examples, and an FPGA (Field Programmable Gate Array).

The number of processors provided for the processing circuitry 40 may be one, two, or more. When plural processors are included in the processing circuitry 40, a memory for storing programs may be provided for each processor or one memory may collectively store all the programs corresponding to the functions of each processor.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An MRI (Magnetic Resonance Imaging) apparatus comprising:
a plurality of receiving coils, each of which includes
(i) an A/D converter configured to convert an MR signal received from an object into a digital signal by sampling the MR signal,
(ii) a clock generation circuit configured to generate a reference clock of the sampling, and
(iii) a radio transmission circuit configured to wirelessly transmit a digitized MR signal; and
a main body configured to wirelessly receive the digitized MR signal and generate an image of the object by reconstructing the digitized MR signal,
wherein one of the plurality of receiving coils is selected as a reference receiving coil by the main body and the selected reference receiving coil is configured to transmit the reference clock generated by the clock generation circuit thereof to each of other receiving coils by radio or by wire; and
each of the other receiving coils is configured to synchronize the reference clock generated by the clock generation circuit thereof with the reference clock transmitted from the selected reference receiving coil.

2. The MRI apparatus according to claim 1, wherein the main body includes processing circuitry configured to determine the reference receiving coil out of the plurality of receiving coils.

3. The MRI apparatus according to claim 2, wherein the processing circuitry is configured to determine the reference receiving coil based on at least one of a position of each of the plurality of receiving coils, a type of each of the plurality of receiving coils, and intensity of an MR signal received by each of the plurality of receiving coils.

4. The MRI apparatus according to claim 2, wherein the processing circuitry is configured to determine the reference receiving coil based on a region of interest set to the object or an imaging region of the object.

5. The MRI apparatus according to claim 3, wherein the plurality of receiving coils includes (a) at least one receiving coil belonging to a first group fixedly arranged on or inside a table for loading the object regardless of contents of an examination and (b) at least one receiving coil belonging to a second group attached to the object according to the contents of an examination; and
the processing circuitry is configured to select the reference receiving coil from the first group.

6. The MRI apparatus according to claim 5, wherein the first group includes at least one of a head coil to be attached to a head of the object and a spine coil to be attached to a back side of the object.

7. The MRI apparatus according to claim 3, wherein each of the plurality of receiving coils is configured to be arranged along a body axis direction of the object; and
the processing circuitry is configured to determine a centermost receiving coil in the body axis direction out of the plurality of receiving coils, as the reference receiving coil.

8. The MRI apparatus according to claim 3, wherein the plurality of receiving coils includes at least one receiving coil belonging to a first group configured to receive an MR signal from a localized region of the object and at least one receiving coil belonging to a second group configured to receive an MR signal from a wide region of the object; and
the processing circuitry is configured to select the reference receiving coil from the first group.

9. The MRI apparatus according to claim 3, wherein the processing circuitry is configured to detect intensity of an MR signal received by each of the plurality of receiving coils and to determine a receiving coil having received an MR signal with strongest intensity as the reference receiving coil.

10. The MRI apparatus according to claim 9, wherein the processing circuitry is configured to determine the reference receiving coil based on intensity of an MR signal received by each of the plurality of receiving coils in a calibration scan performed before a main scan.

11. The MRI apparatus according to claim 4, wherein the processing circuitry is configured to determine a receiving coil closest to the region of interest set to the object out of the plurality of receiving coils, as the reference receiving coil.

12. The MRI apparatus according to claim 4, wherein the processing circuitry is configured to determine a receiving coil closest to an imaging region of the object out of the plurality of receiving coils, as the reference receiving coil.

13. The MRI apparatus according to claim 12, wherein the processing circuitry is configured to switch the reference receiving coil when the imaging region is changed during imaging, in such a manner that a receiving coil closest to a changed imaging region is newly selected as the reference receiving coil according to movement of the imaging region.

14. The MRI apparatus according to claim 12, wherein the processing circuitry is configured to set a slab and/or a slice of the object as the imaging region of the object.

15. The MRI apparatus according to claim 2, wherein the main body is configured to store a look-up table in which one receiving coil to be selected as the reference receiving coil is preliminarily assigned to each of combinations of an imaging part of the object and at least one receiving coil to be used for the imaging part; and
the processing circuitry is configured to refer to the look-up table and to determine one receiving coil assigned to a combination of the imaging part and at least one receiving coil set as imaging conditions, as the reference receiving coil.

16. The MRI apparatus according to claim 1, wherein each of the plurality of receiving coils further includes a memory configured to temporarily store the MR signal; and
each of the plurality of receiving coils is configured to read out the MR signal from the memory and wirelessly transmit the MR signal to the main body at a predetermined timing.

17. The MRI apparatus according to claim 16, wherein each of the plurality of receiving coils is configured to
(a) add an identification number to data of the MR signal,
(b) store the data of the MR signal with the identification number in the memory, and
(c) when transmission of the data fails, retransmit the failed data stored in the memory to the main body, based on the identification number.

18. The MRI apparatus according to claim 1, wherein the reference receiving coil is configured to further transmit the reference clock to the main body.

19. The MRI apparatus according to claim 1, wherein the reference receiving coil is configured to instruct other receiving coils about a timing of transmitting the MR signal to the main body.

20. The MRI apparatus according to claim 1, wherein the reference receiving coil is configured to acquire MR signals received by other receiving coils and then transmit the acquired MR signals to the main body.

* * * * *